US012343447B2

(12) United States Patent
Bonfanti et al.

(10) Patent No.: US 12,343,447 B2
(45) Date of Patent: Jul. 1, 2025

(54) METHODS FOR TISSUE DECELLULARIZATION

(71) Applicant: UCL BUSINESS LTD, London (GB)

(72) Inventors: Paola Bonfanti, London (GB); Asllan Gjinovci, London (GB)

(73) Assignee: UCL BUSINESS LTD, London (GB)

( * ) Notice: Subject to any disclaimer, the term of this patent is extended or adjusted under 35 U.S.C. 154(b) by 1047 days.

(21) Appl. No.: 17/055,328

(22) PCT Filed: May 14, 2019

(86) PCT No.: PCT/GB2019/051310

§ 371 (c)(1),
(2) Date: Nov. 13, 2020

(87) PCT Pub. No.: WO2019/220091

PCT Pub. Date: Nov. 21, 2019

(65) Prior Publication Data

US 2021/0187164 A1 Jun. 24, 2021

(30) Foreign Application Priority Data

May 14, 2018 (GB) ..................................... 1807788

(51) Int. Cl.

| | |
|---|---|
| ***A61L 27/36*** | (2006.01) |
| ***A61L 27/38*** | (2006.01) |
| ***C12N 5/00*** | (2006.01) |
| ***C12N 5/0775*** | (2010.01) |
| ***C12N 5/078*** | (2010.01) |
| ***G01N 33/50*** | (2006.01) |

(52) U.S. Cl.

CPC ....... *A61L 27/3687* (2013.01); *A61L 27/3633* (2013.01); *A61L 27/3813* (2013.01); *A61L 27/3834* (2013.01); *A61L 27/3886* (2013.01); *C12N 5/0068* (2013.01); *C12N 5/0634* (2013.01); *C12N 5/0662* (2013.01); *G01N 33/5088* (2013.01); *C12N 2502/11* (2013.01); *C12N 2502/13* (2013.01); *C12N 2533/90* (2013.01)

(58) Field of Classification Search

CPC ............. A61L 27/3687; A61L 27/3633; A61L 27/3813; A61L 27/3834; A61L 27/3886; C12N 5/0068; C12N 5/0634; C12N 5/0662; C12N 2502/11; C12N 2502/13; C12N 2533/90; G01N 33/5088

See application file for complete search history.

(56) References Cited

U.S. PATENT DOCUMENTS

2010/0093066 A1 4/2010 Taylor et al.
2013/0344490 A1* 12/2013 Kim ..................... C12N 5/0693 435/395
2014/0300293 A1 10/2014 Ruan et al.
2016/0030637 A1 2/2016 Ross et al.

FOREIGN PATENT DOCUMENTS

| | | | | |
|---|---|---|---|---|
| CN | 107096070 A * | 8/2017 | ......... A61L 27/3604 |
| JP | 2009-505752 A | 2/2009 | |
| JP | 2015-510391 A | 4/2015 | |
| JP | 2016-513654 A | 5/2016 | |
| WO | WO 2007/025233 A1 | 3/2007 | |
| WO | WO 2013/096741 A2 | 6/2013 | |

OTHER PUBLICATIONS

Jiang, J., et al., "Surgical technique for vascularized thymus transplantation in mice," Microsurgery 19(2): 56-60. (Year: 1999).*

Campo et al., "De-and recellularization of the pig uterus: a bioengineering pilot study," *Biology of Reproduction* 96(1): 34-45 (Dec. 20, 2016).

Fan et al., "Bioengineering thymus organoids to restore thymic function and induce donor-specific immune tolerance to allografts," *Molecular Therapy* 23(7): 1262-1277 (Jul. 1, 2015).

Goh et al., "Perfusion-decellularized pancreas as a natural 3D scaffold for pancreatic tissue and whole organ engineering," *Biomaterials* 34(28): 6760-6772 (Jun. 17, 2013).

Hun et al., "Native thymic extracellular matrix improves in vivo thymic organoid T-cell output, and drives in vitro epithelial cell differentiation," *Biomaterials* 118: 1-15 (Nov. 30, 2016).

International Search Report and Written Opinion from parent PCT Application No. PCT/GB2019/051310, 15 pages (mailed Jul. 29, 2019).

Pan et al., "Regeneration of a Bioengineered Thyroid Using Decellularized Thyroid Matrix," *Thyroid Matrix* 29(1): 142-152 (Jan. 23, 2019).

* cited by examiner

*Primary Examiner* — Tracy Vivlemore
*Assistant Examiner* — Eric J Rogers
(74) *Attorney, Agent, or Firm* — Klarquist Sparkman, LLP

(57) ABSTRACT

The present invention provides A method of producing a decellularised extracellular matrix (ECM) scaffold of at least a portion of a lobular organ with no common artery, the method comprising: a) closing afferent blood vessels to substantially seal a target lobular organ or portion thereof with no common and/or major artery within a non-human donor or a dead/brain dead human donor; b) optionally: (i) cleaning coagulum and/or blood from at least a portion of the closed afferent blood vessels; and/or (ii) perfusing the organ or portion thereof to confirm closure of the afferent blood vessels; c) removing the sealed organ or portion thereof from the donor; and d) perfusing the sealed organ or portion thereof with detergent and enzymatic solutions to obtain the decellularised ECM scaffold. Methods for producing an artificial organ, and artificial organs produced by the methods are also provided.

15 Claims, 14 Drawing Sheets

METHODS FOR TISSUE DECELLULARIZATION

CROSS REFERENCE TO RELATED APPLICATIONS

This is the U.S. National Stage of International Application No. PCT/GB2019/051310, filed May 14, 2019, which claims the benefit of Great Britain Application No. 1807788.3, filed May 14, 2018.

FIELD OF INVENTION

The present invention relates to methods for producing a decellularised extracellular matrix (ECM) scaffold of a lobular organ with no common artery and/or major artery, scaffolds obtained or obtainable by such methods, methods for repopulating the scaffolds and artificial organs comprising the scaffolds.

BACKGROUND TO THE INVENTION

Organ transplantation is an essential life-saving treatment for many patients. However, despite increasing numbers of organ donors it is still not possible to meet the demand for organs. Figures from the National Health Service indicate that in the United Kingdom 411 patients died while on the active waiting list for a transplant between March 2016 and March 2017. Donors and recipients have to be tissue matched to reduce the likelihood of transplant rejection and, even then, the vast majority of recipients require immunosuppression for the rest of their lifespan, which can result in complications such as increased risk of infections or damage to other organs.

Organ bioengineering, involving seeding cells on supporting scaffolds, is a developing area in the field of organ transplantation. Currently, successful construction and transplantation of simple organs such as blood vessels, bladders, airways and urethras has been possible. Typically, construction of these organs involves seeding autologous cells onto simple biomaterial scaffolds. Due to their structural simplicity (including hollow cores and thin walls), once implanted into a patient these artificial organs can be supported by diffusion of oxygen and nutrients from adjacent tissues until angiogenesis occurs. However, more complex organs cannot be supported by diffusion and require connection to the recipient's blood supply, posing the challenge of developing artificial organs that include afferent and efferent blood vessels.

One potential solution to this problem that has been suggested in relation to kidney transplants is the use of intact scaffolds produced from the extracellular matrix (ECM) of human or animal kidneys. Donor kidneys were decellularised using detergent perfusion through the renal artery and produced ECM scaffolds with an intact vascular network as well as preserving various structural proteins and three-dimensional architecture (Katari et al 2014). While the scaffolds show promise in the development of artificial kidneys the authors concluded that seeding and growth of cells on the scaffold was not yet adequately enabled to a level to allow artificial kidneys to be produced for implantation. Perfusion-decellularisation of the pancreas has been performed by catheterisation of the anterior hepatic portal vein, which is formed by the confluence of the splenic and superior mesenteric veins (Goh et al 2013). The authors note that attempts to perfuse the organ through other circulatory systems, such as the pancreatic duct, were not successful in producing a viable decellularised ECM scaffold.

Decellularising ECM scaffolds shows promise in the development of artificial organs, but significant technical challenges remain, particularly for organs with a complex structure, such as those having a lobular structure and lacking a common artery and/or major artery. One such organ is the thymus, which is formed of two lobes, each of which receives blood supply from branches derived from the thyroid inferior artery and the internal thoracic mammary artery. Due to the lack of a common or major artery or vein or duct supplying the organ it is not possible to use the perfusion-decellularisation approach utilised in relation to organs such as the kidney or the pancreas. To date, it has only been possible to obtain thymus scaffolds by mechanically shaking or rotating the organ in a detergent solution, which has resulted poor characterisation of the whole scaffold and failed to maintain the fine reticular and vasculature structure (Fan et al 2015).

SUMMARY OF THE INVENTION

Lobular organs with no common artery typically develop as separate lobes which migrate into their final location as independent vascularised structures, after which the lobes may adhere to each other through a layer of connective tissue. Due to the lack of a common arterial supply to the whole organ, or indeed sometimes to the lobes thereof, it has not been possible to apply a perfusion-decellularisation approach to obtaining ECM scaffolds from these organs. However, the present inventors have developed a technique that allows whole organ perfusion of such lobular organs. The method of the invention creates an artificial perfusion system by closing afferent blood vessels, which allows a perfusion-decellularisation approach to be applied to the organ.

Accordingly, in a first aspect the present invention provides a method of producing a decellularised extracellular matrix (ECM) scaffold of at least a portion of a lobular organ with no common artery; the method comprises: a) closing afferent blood vessels to substantially seal a target lobular organ, or portion thereof, with no common and/or major artery within a non-human donor or a dead/brain dead human donor; b) optionally: (i) cleaning coagulum and/or blood from at least a portion of the closed afferent blood vessels; and/or (ii) perfusing the organ or portion thereof to confirm closure of the afferent blood vessels; c) removing the sealed organ or portion thereof from the donor; and d) perfusing the sealed organ or portion thereof with detergent and enzymatic solutions to obtain the decellularised ECM scaffold. The novel artificial perfusion system approach provided by the method of the present invention allows decellularised ECM scaffolds to be obtained from lobular organs with no common artery while preserving the fine reticular structure of the ECM including the vascular network. In embodiments of the invention the ECM scaffold is obtained from a portion of the lobular organ, such as one lobe or gland, said lobe or gland lacking a common arterial supply.

In an embodiment of the invention, the target organ or portion thereof may be removed from a live human donor prior to steps a-d above being carried out. The decellularised ECM scaffold obtained in this embodiment of the invention may be utilised as outlined below.

Substantially sealing the target organ, or portion thereof, means that key blood vessels supplying the organ or lobe are closed, thereby creating an artificial perfusion system. Typically, one or two blood vessels will be left open for subsequent cannulation to allow perfusion of the organ. Preferably only one blood vessel is left open for subsequent cannulation. Suitable techniques for closing blood vessels will be familiar to those skilled in the art. For example, the afferent blood vessels may be clamped, sutured or plugged. In preferred embodiments of the invention the afferent blood vessels are ligated.

The donor may be a non-human donor, preferably a non-human mammal, such as a pig. Alternatively the donor may be a dead/brain dead human donor, such as a brain dead, heart-beating, respirated potential organ donor. The human donor may be a paediatric, adult or geriatric donor. Since the source of the scaffold may be allogeneic or xenogeneic, maximal decellularisation is desirable. However, this must be balanced against the need to preserve ECM integrity and bioactivity as the ECM has been shown to affect cell migration, proliferation and differentiation. The three-dimensional structure, surface topology and composition of the ECM all contribute to these effects. While the term decellularisation has not been fully defined by quantitative metrics, some minimal criteria have been proposed, which include less than 50 ng dsDNA per mg ECM dry weight, less than 200 bp DNA fragment length, and/or the lack of visible nuclear material in histologic staining of the tissue. The decellularised ECM produced by the method of the present invention may satisfy any one or more of these criteria.

As explained above, the method of the present invention optionally includes a step of cleaning coagulum and/or blood from at least a portion of the closed afferent blood vessels. This can be done by washing the blood vessels with an inert buffer such as phosphate buffered saline (PBS). Removing coagulum and/or blood from the closed afferent blood vessels helps to ensure that the artificial perfusion system that has been created is free from any blockages and can subsequently be freely perfused with detergent.

The method may additionally or alternatively include a step of perfusing the sealed organ or portion thereof to confirm closure of the afferent blood vessels. Typically this perfusion will be performed by cannulation of an afferent blood vessel that has not been closed during the step of sealing the organ or portion thereof. This perfusion step can be carried out using an inert buffer such as PBS and can be used to identify any additional afferent blood vessels that may still need to be closed, for example, due to anatomical variations between individual donors. The perfusion step may additionally be beneficial in identifying any incomplete closures of blood vessels, which could be detrimental to the artificial perfusion that has been created by their closure and thereby allowing this to be rectified prior to perfusion-decellularisation of the target organ or portion thereof.

A number of suitable detergent and enzymatic solutions can be used for perfusion-decellularisation of the target organ or portion thereof. In particular, the detergent may be selected from one or more of sodium deoxycholate (SDC), sodium dodecyl sulphate (SDS) and Triton X-100. In preferred embodiments of the invention the detergent is SDC, which has been shown to produce decellularised ECM scaffolds that retain the fine native reticular structure and vasculature of the ECM. Additionally, this detergent is not toxic and can simply be washed out with water after the perfusion-decellularisation cycle or cycles are complete. In contrast, SDS may require removal with a further detergent.

Detergent concentration can be optimised based on the volume of the organ or portion thereof to be perfused, the duration of the perfusion cycle or cycles and the perfusion rate. For example, the organ or portion thereof may be perfused with about 1% to about 10% (w/v) SDC, preferably about 1% to about 7% (w/v), more preferably about 2% to about 6% (w/v) SDC. In preferred embodiments of the invention the organ or portion thereof may be perfused with about 4% (w/v) SDC. Alternatively, the organ or portion thereof may be perfused with about 0.05% to about 1% (w/v) SDS, preferably about 0.05% to about 0.5% (w/v), more preferably the organ or portion thereof may be perfused with about 0.1% (w/v) SDS. The organ or portion thereof may be perfused with about 0.05% to about 5% (w/v) Triton X-100, preferably about 0.1% to about 2% (w/v), more preferably the organ or portion thereof may be perfused with about 1% (w/v) Triton X-100. In embodiments of the invention where the detergent used for perfusion-decellularisation of the organ or portion thereof is SDS the organ or portion thereof may be washed with another detergent, such as Triton X-100, once the perfusion-decellularisation step is complete.

Detergent and enzymatic solutions as used in the present invention preferably comprise one or more enzymes such as an endonuclease (for example, Deoxyribonuclease I) or a protease (for example, trypsin). The detergents and enzymes may be provided in separate solutions or may be combined in a single solution.

Perfusion-decellularisation of the organ or portion thereof preferably utilises detergent-enzymatic treatment (DET), which will be familiar to the skilled person. As discussed above, key afferent blood vessels supplying the target lobular organ or portion thereof with no common artery are closed to substantially seal the organ or portion thereof, with one or two vessels being left open for subsequent cannulation for perfusion of the organ or portion thereof. The detergent and enzymes are therefore perfused into the organ or portion thereof through the open blood vessel(s). Typically, the organ or portion thereof is perfused for about 1 to about 4 hours, preferably about 1 to about 2 hours. In embodiments of the invention the organ or portion thereof may require detergent perfusion for only about 1.5 hours.

The sealed organ or portion thereof may be perfused with detergent at a rate of from about 0.2 ml/min to about 1 ml/min, preferably about 0.5 ml/min to about 0.9 ml/min. In preferred embodiments of the invention the organ or portion thereof may be perfused at a rate of about 0.6 to about 0.8 ml/min.

In embodiments of the invention the sealed organ or portion thereof may be perfused for a single cycle, which has been shown to avoid the formation of precipitates in the fine blood vessels. For example, the organ or portion thereof may be perfused with detergent for a single cycle of about 1.5 hours. Alternatively, a second cycle of detergent perfusion may be used so that the organ or portion thereof is perfused for two cycles of about 1.5 hours each.

The sealed organ or portion thereof may be freely floating in solution during perfusion, which has been shown to reduce tension and avoid the risk of a catheter or cannula contacting a blood vessel wall. However, in alternative embodiments of the invention the organ or portion thereof may simply be submerged in a suitable container and does not have to be freely floating. The organ or portion thereof may be perfused in bioreactor or in a closed system.

As explained above, the lobular organ with no common and/or major artery is an organ that develops as separate lobes which migrate into their final location as independent vascularised structures. Such organs include the thymus, the thyroid gland, the parathyroid gland and the salivary glands. Due to the lack of a common arterial supply to the whole organ, or indeed to specific portions thereof, such as lobes or glands, it has not previously been possible to apply a perfusion-decellularisation approach to obtaining ECM scaffolds from these organs or portions thereof.

The thymus consists of two lobes, merged in the middle and surrounded by a capsule that extends with blood vessels into the interior. The lobes consist of a dense outer cortex and an inner less dense medulla. In the two lobes, hematopoietic precursors from the bone-marrow, referred to as thymocytes, mature into T cells. Once mature, T cells emigrate from the thymus and make up the peripheral T cells responsible for directing many parts of the adaptive immune system. Loss of the thymus at an early age through chromosomal abnormality (as in DiGeorge syndrome) results in severe immunodeficiency and subsequent high susceptibility to infection. The thymus lacks a common artery to supply blood to the whole organ and instead receives blood supply from branches of the internal thoracic (also known as the internal mammary) and inferior thyroid arteries, with branches from the superior thyroid artery sometimes seen. The blood vessels closed to seal the thymus may include the right or left common carotid artery, the right subclavian artery, the right internal mammary artery, the right costocervical trunk, the right aortic arch, the left aortic arch, the left costocervical trunk, the left internal mammary artery. As explained above, one or two blood vessels are left open for subsequent perfusion of the organ. In preferred embodiments of the invention only one blood vessel is left open. For example, when the right common carotid artery is closed the thymus may be perfused through the left common carotid artery, or when the left common carotid artery is closed the thymus may be perfused through the right common carotid artery.

The thyroid gland is a butterfly-shaped organ that sits at the front of the neck in humans. It is composed of two lobes, left and right, connected by a narrow isthmus. The primary function of the thyroid is the production of the iodine-containing thyroid hormones, triiodothyronine (T3) and thyroxine (T4) and the peptide hormone calcitonin. The thyroid hormones have a wide range of effects on the human body, which include metabolic, cardiovascular, developmental effects, as well as playing a role in maintaining normal sexual function, sleep, and thought patterns. The thyroid lacks a common artery to supply blood to the whole organ and instead receives blood supply from the inferior thyroid artery, a branch of the thyrocervical trunk of the subclavian artery, and from the superior thyroid artery, branch of the external carotid artery and, sometimes by the thyroid Ima artery, which can vary in size from very small to the size of the inferior thyroid artery. The blood vessels closed to seal the thyroid may include the right or left common carotid artery after junction with superior thyroid artery. When the two lobes of the thyroid are connected by blood vessels passing through the isthmus it may be possible to utilise the method of the present invention to decellularise the ECM scaffold of the whole organ. Alternatively, the method may be applied to a single lobe of the thyroid to produce a decellularised ECM scaffold of the lobe. Each thyroid lobe may be perfused through the right or left common carotid artery.

There are typically four parathyroid glands in humans, divided into two pairs of glands usually positioned behind the left and right lobes of the thyroid. The two parathyroid glands on each side which are positioned higher are called the superior parathyroid glands, while the lower two are called the inferior parathyroid glands. The major function of the parathyroid glands is to maintain the body's calcium and phosphate levels within a very narrow range, so that the nervous and muscular systems can function properly. Blood supply to the parathyroid glands corresponds to the overlying thyroid gland, and each parathyroid gland lacks a common or major artery. The decellularisation method of the present invention may be applied to an individual parathyroid gland.

The salivary glands in mammals are exocrine glands that produce saliva through a system of ducts. Humans have three paired major salivary glands (parotid, submandibular, and sublingual) as well as hundreds of minor salivary glands. The major salivary glands each lack a common or major artery. The decellularisation method of the present invention may be applied to a parotid gland, a submandibular gland or a sublingual gland.

The present invention also provides a decellularised ECM scaffold obtained or obtainable by the method of the present invention. The method of the present invention has been demonstrated to result in a high degree of preservation of the architecture and vasculature of the ECM, while achieving successful decellularisation of a lobular organ having no common artery. The method may be applied to a whole organ or to a portion thereof, such as a lobe or gland.

In a further aspect the present invention provides a method for producing an artificial organ, the method comprising repopulating a decellularised ECM scaffold obtained or obtainable by the method of the present invention with stromal cells, such as a combination of epithelial and mesenchymal cells, culturing the repopulated scaffold in vitro for about 4 to about 7 days and then optionally seeding the repopulated scaffold with donor cells.

The decellularised ECM scaffold may be repopulated with epithelial and mesenchymal cells at a ratio of about 2:1 to about 5:1. Preferably, the scaffold is repopulated with epithelial and mesenchymal cells at a ratio of about 5:1. The stromal cells are typically obtained by ex vivo expansion of cells from an organ tissue donor (i.e. allogeneic or xenogeneic cells) and may be delivered to the scaffold by direct needle injection, which provides successful distribution of cells onto and/or inside the scaffold. However, in embodiments of the invention the stromal cells may by autologous cells. The cells may be delivered separately, simultaneously or sequentially. Sequential delivery may involve delivering the cell populations within at least 1, 2, 5, 10, 20, 30, 40, 50 or 60 minutes of each other, or within 1, 2, 3, 4, 5, 6, 7, 8, 9, 10, 11, 12, 14, 36 or 48 hours of each other. However, in preferred embodiments of the invention the epithelial cells and mesenchymal cells are delivered simultaneously, either from separate sources or pre-mixed together in a suitable ratio as described above. Typically the cells are injected in the form of a cell suspension, which contains a mixture of epithelial and mesenchymal cells at a ratio of about 2:1 to about 5:1 and which may have a volume of about 10 μl to about 100 μl, preferably about 10 μl to about 60 μl, more preferably about 30 μl to about 40 μl. For example, a single injection may contain a suspension of about $2\times10^6$ epithelial cells and about $0.4\times10^6$ mesenchymal cells in a volume of about 30 μl to about 40 μl.

Repopulation of a decellularised ECM scaffold with endothelial cells, optionally in combination with mesenchymal cells, is an important step in revascularisation of the scaffold. For example, endothelial cells (preferably including pericyte-like cells) and mesenchymal cells may be injected at multiple sites of the scaffold. Alternatively, endothelial cells (preferably including pericyte-like cells) and mesenchymal cells may be injected into one or more afferent blood vessels to revascularise the scaffold. The cells may be injected as a composition, with the volume of the injection(s) being optimised to fill the volume of the scaffold. Similarly, the concentration of cells in the composition may be optimised based on the volume of the composition, in order to ensure that a sufficient number of cells is injected to fully revascularise the scaffold.

The repopulated scaffolds are typically maintained in vitro to allow for cell migration over the reticular ECM of the scaffold and initial differentiation (e.g. cell polarisation, up/downregulation of adhesion molecules) over a period of about 4 to about 7 days. Donor cells from different origins (typically allogeneic or xenogeneic cells, but optionally could be autologous) can then be delivered, e.g. by direct needle injection into or onto previously injected scaffold areas. For example, the donor cells may be stem cells such as haematopoietic stem cells (HSC), including $Lin^-/CD45^+/CD3^-/CD4^-/CD8a^-$ thymocytes from postnatal thymus, $CD34^+$ cells from foetal liver, $CD34^+$ cells from cord blood (CBC), $CD34^+$ cells from adult bone marrow or $CD34^+$ cells from mobilized peripheral blood (adult). The donor cells may be iPSC-derived stromal cells and/or endothelial cells, optionally in combination with HSC or T-cell progenitors and could be patient-specific (i.e., autologous). Alternatively, the donor cells may be derived from any lineage (e.g., endoderm, mesoderm or neural crest) and may include thymocytes, thymic epithelial cells, mesenchymal cells, dendritic cells, endothelial cells, pericytes, macrophages or B cells. Typically the organ is maintained in vitro for a further 24 hours or more after delivery of the donor stem cells and prior to implantation into a recipient. It will be appreciated that the scaffold may need not be entirely populated with the seeded cells to be useful for implantation into a subject. For example, the scaffold may have seeded cells across at least 70, 80, 90, 95 or 99% of its surface.

Optionally, in vitro expanded endothelial cells may additionally be delivered to the organ prior to implantation into a recipient. Without being bound by theory, it is believed that such cells contribute to accelerated vascularisation of the organ after implantation. Indeed, such endothelial cells can be delivered to the organ through the artificial perfusion system created when producing the scaffold. Such delivery of the endothelial cells can help to re-endothelialise the vascular tree of the organ. Optionally, the donor stem cells may be delivered by the same route.

In an alternative embodiment of the invention, the decellularised ECM scaffold may be repopulated with stromal cells to form a repopulated scaffold that can be implanted into a recipient. Once implanted into the recipient the repopulated scaffold is vascularised and may be subsequently repopulated with autologous stem cells, such as HSC, directly in vivo from the blood circulation. Mesenchymal and/or immune cells resident in the site of the implantation may also invade the scaffold and help the remodelling and/or support seeded cell survival and/or differentiation and functionality. The repopulated scaffold may have seeded cells across at least 70, 80, 90, 95 or 99% of its surface prior to implantation.

The decellularised ECM scaffolds or repopulated ECM scaffold as described above may additionally be treated to enhance adherence of cells to the scaffold and/or growth of cells on the scaffold. Such treatments may include the application of proteins such as growth factors or extracellular matrix proteins, for example, including one or more of collagen, elastin, fibronectin, laminin, or proteoglycans. In embodiments of the invention the cells seeded on the scaffold might be modified to produce growth factors, such as VEGF, that will allow faster vascularisation. Modification of the cells typically refers to genetic modification of the cells and may utilise standard techniques known in the art An artificial organ comprising a decellularised ECM scaffold obtained or obtainable by the method of the present invention is also provided. The artificial organ may be produced by repopulating a decellularised ECM scaffold of the present invention with stromal cells as described above. The artificial organ may be for use in therapy, for example, to provide replacement organs to treat congenital or acquired conditions.

As explained above, the cells used to repopulate the decellularised ECM scaffold of the present invention can be obtained from donor tissue which is cultivated to provide the desired cell types and which can be expanded in vitro prior to being seeded onto the scaffold. In this way a single tissue donor can provide multiple artificial organs. As the cells grown on the scaffold are key to any potential immunogenicity of the artificial organ (as cells have been removed from the scaffold the scaffold itself is not immunogenic and therefore does not have to be obtained from a tissue matched donor) this provides an important advantage where there is particular shortage of suitable tissue donors.

The artificial organ comprising a decellularised ECM scaffold obtained or obtainable by the method of the present invention may be a thymus and may be used to treat conditions such as DiGeorge syndrome, which is a congenital chromosomal disorder that causes a number of symptoms including an absent or hypoplastic thymus, leading to severe immunodeficiency. Artificial organs of the present invention may alternatively be used as a source of mature cells for adoptive cell transfer, i.e. for the production of therapeutic cells, such as T-cells.

In a further aspect the present invention provides an in vitro method for testing a compound for its ability to elicit a pharmacological, immunological or toxicological response, the method comprising contacting an artificial organ comprising a decellularised ECM scaffold of the present invention with the compound.

The artificial organ may be cultured in vitro for up to 1, 2, 3, 4, 5 or 6 days. In embodiments of the invention the artificial organ may be cultured in vitro for up to 1, 2, 3, 4, 5, 6, 7, 8, 9 or 10 weeks. Preferably the artificial organ is cultured in vitro for up to 8 weeks. The artificial organ may be cultured under standard culture conditions. However, in preferred embodiments of the invention the artificial organ is perfused with cell culture medium during the culture period, e.g. by culturing the organ in a bioreactor.

The present additionally provides a method of organ transplantation, the method comprising surgically implanting an artificial organ comprising a decellularised ECM scaffold of the present invention into a patient. A method of treating a disease, the method comprising surgically implanting an artificial organ comprising a decellularised ECM scaffold of the present invention into a patient in need thereof is also provided. In particular the artificial organ comprising a decellularised ECM scaffold of the present invention can be used for inducing immune tolerance in regular organ transplantation.

The term “patient” or “recipient” as used herein may include any mammal, including a human. Particularly, the patient may be a paediatric patient such as a neonate or an infant. The patient may be suffering from an acquired or congenital disorder requiring replacement of an organ. For example, the organ may be missing, diseased, damaged or its function may be otherwise impaired. The patient may have received a transplant of another organ prior to or concurrently with receiving an artificial organ comprising the decellularised ECM scaffold of the present invention. Without being bound by theory, it is believed that cells repopulating the decellularised ECM scaffold (e.g. AIRE+ cells) could provide Treg cells and induce donor-organ tolerance.

BRIEF DESCRIPTION OF THE DRAWINGS

The invention will now be described in detail, by way of example only, with reference to the figures.

EXAMPLES

Example 1

Figure 1:
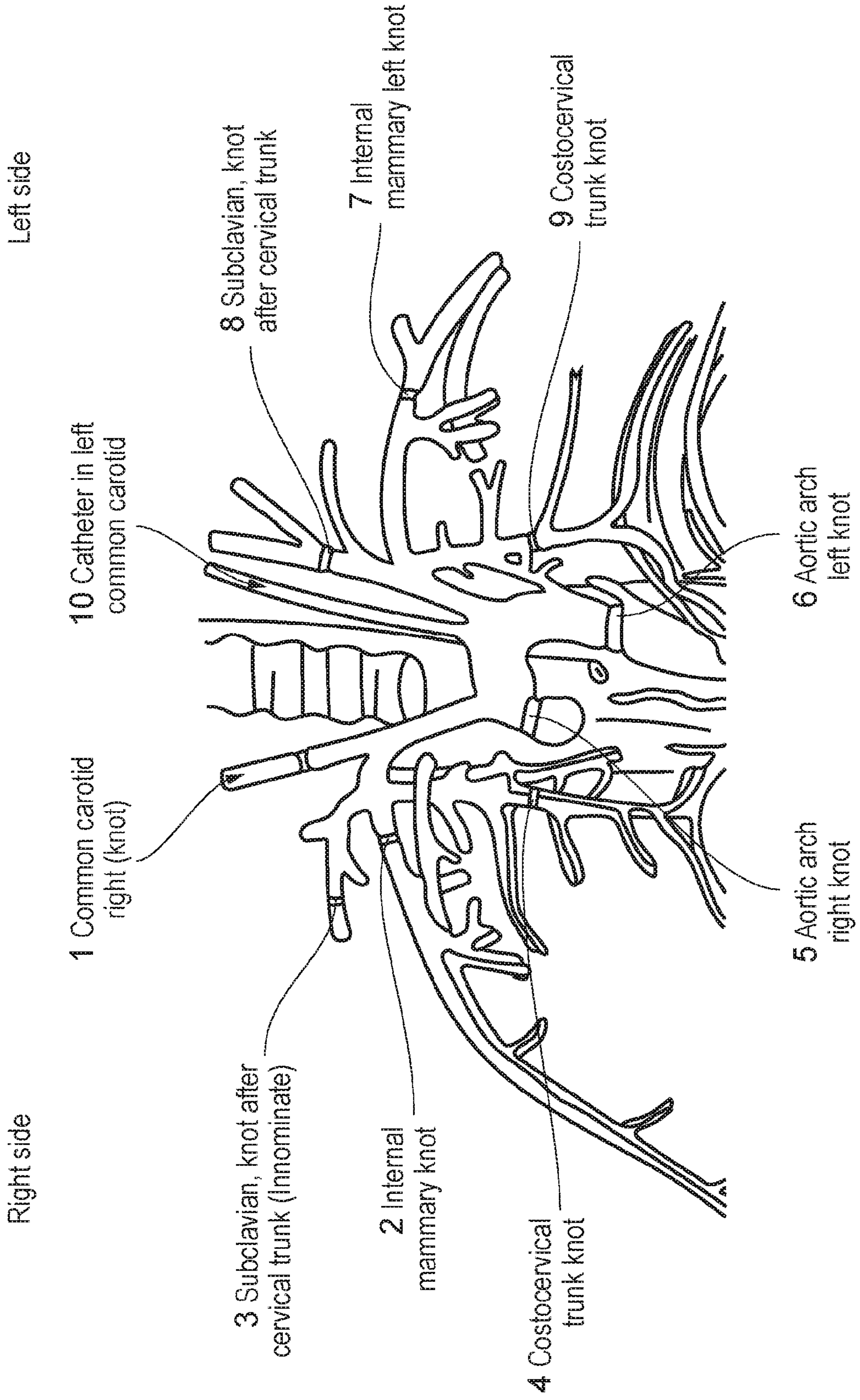
FIG. 1 shows a schematic representation of a surgical procedure for ligating specific artery branches that allow the formation of an artificial perfusion system around the thymus. Knots 1-9 are formed in the afferent blood vessels (knot 6 on the left aortic arch should not be tight at this stage), then the catheter is inserted into the left common carotid. The left internal jugular vein is incised; followed by incision of the left aortic arch below knot 6; then the right internal jugular vein is cut. Buffer solution, such as PBS, is flushed slowly through the catheter to wash the aortic arch and remove coagulum, then knot 6 on the left aortic arch is closed tightly. The cannulated/catheterised thymus is then removed by cutting the closed arteries near knots 1-9, then the associated veins are cut starting from the subclavian vein.

Rat thymi were sealed by ligating the right common carotid artery, the right subclavian artery, the right internal mammary artery, the right costocervical trunk, the right aortic arch, the left aortic arch, the left costocervical trunk, the left internal mammary artery and the left subclavian artery (see FIG. 1) and were then extracted from subjects. The sealed thymi were decellularised in parallel using the following detergent-enzymatic perfusion treatment (DET), which was perfused by cannulation of the left common carotid artery while freely floating in solution:

a. perfusion with MilliQH2O for 96 hrs at 0.2 mL/min, 4° C.;
b. perfusion with 4% SDC for 1.5 h at 0.2 mL/min, RT;
c. perfusion with MilliQH2O for 24 hrs at 0.2 mL/min, RT;

d. perfusion with 0.1 mg/ml DNase (warm 37° C.) at 0.2 mL/min for 30 min; and e. perfusion with PBS at 0.2 mL/min for 1 hr, RT.

The scaffolds were then processed for sterilization (gamma irradiation, 1782Gy).

Figure 2A:
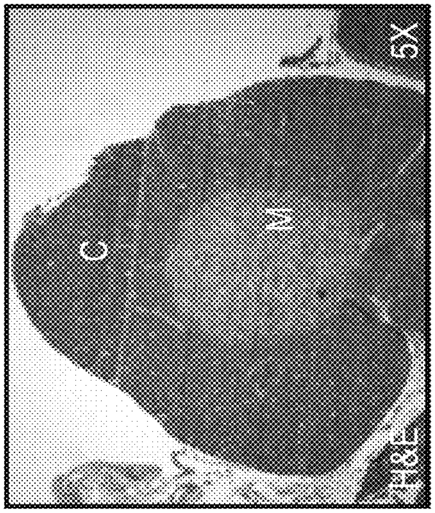
FIGS. 2A-2D show rat thymi before (A,B) and after (C,D) decellularisation through perfusion of detergent and enzymatic solutions (DET) at both gross macroscopy (B,D) and by histology (Haematoxylin and Eosin, H&E; A, C).
Figure 2B:
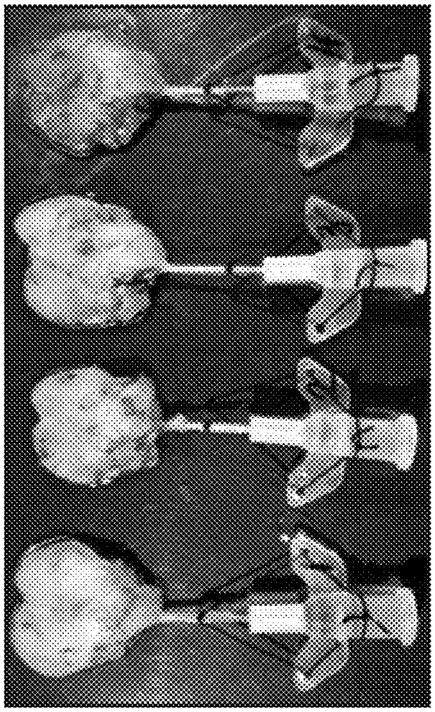
Figure 2C:
Figure 2D:
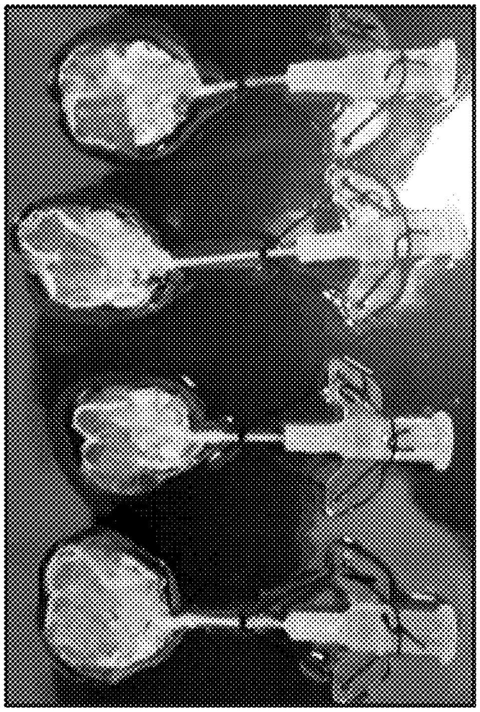
Figure 3A:
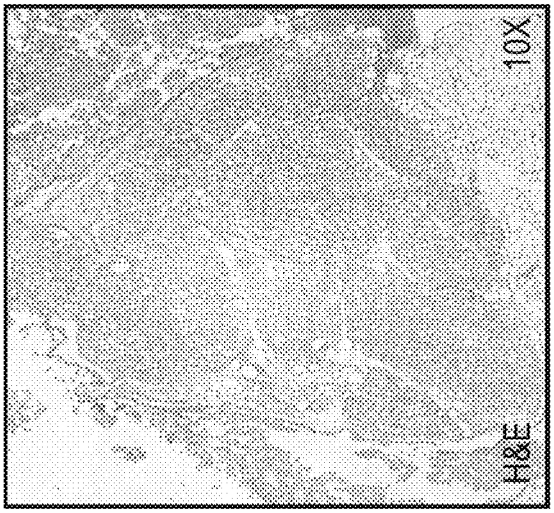
FIGS. 3A-3C show the histology of decellularised thymus scaffold of the present invention: Haematoxylin and Eosin (H&E) (A), Picrosirius Red (collagen, B) and Masson's Trichrome (ECM, C) staining demonstrate the absence of cell nuclei and preservation of capsular and reticular ECM of the thymus.
Figure 3B:
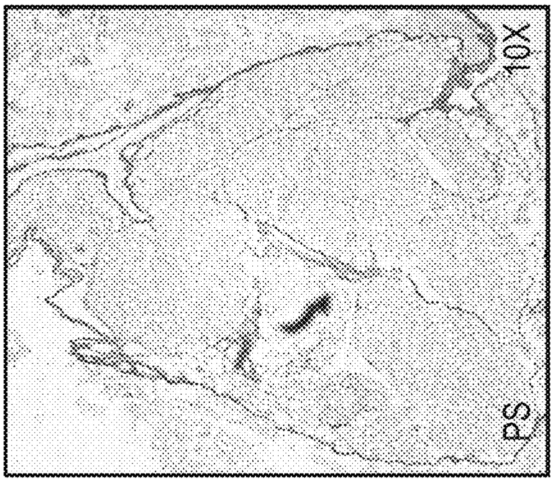
Figure 3C:
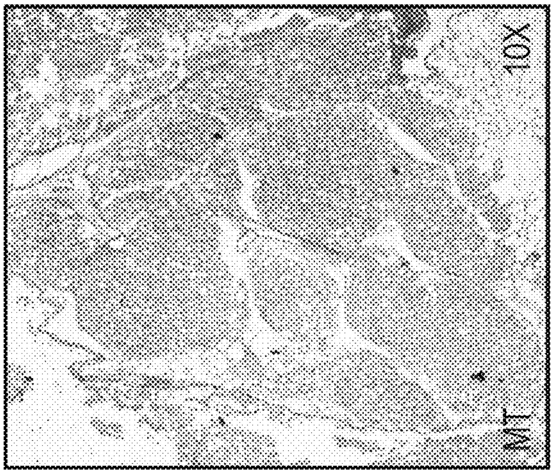
Figure 4A:
FIGS. 4A-4D show gross microscopy of a rat thymus scaffold before (panel A) and after (panel B) decellularisation by the method of the present invention. H&E staining of the thymus at low magnification (4×, panel C) and at higher magnification (panel D, scale bar=100 um), demonstrates preservation of parenchymal lobular and vascular structures.
Figure 4B:
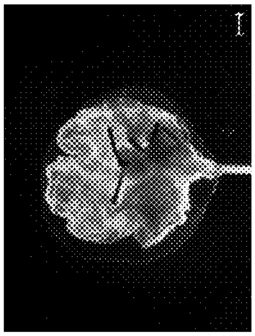
Figure 4C:
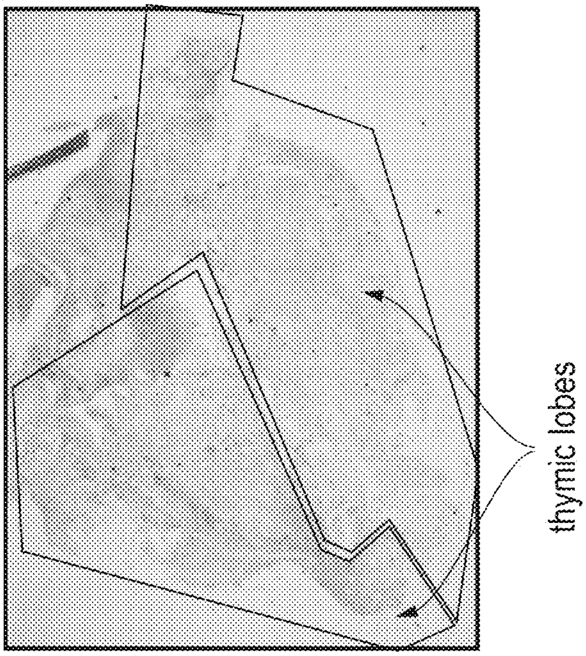
Figure 4D:
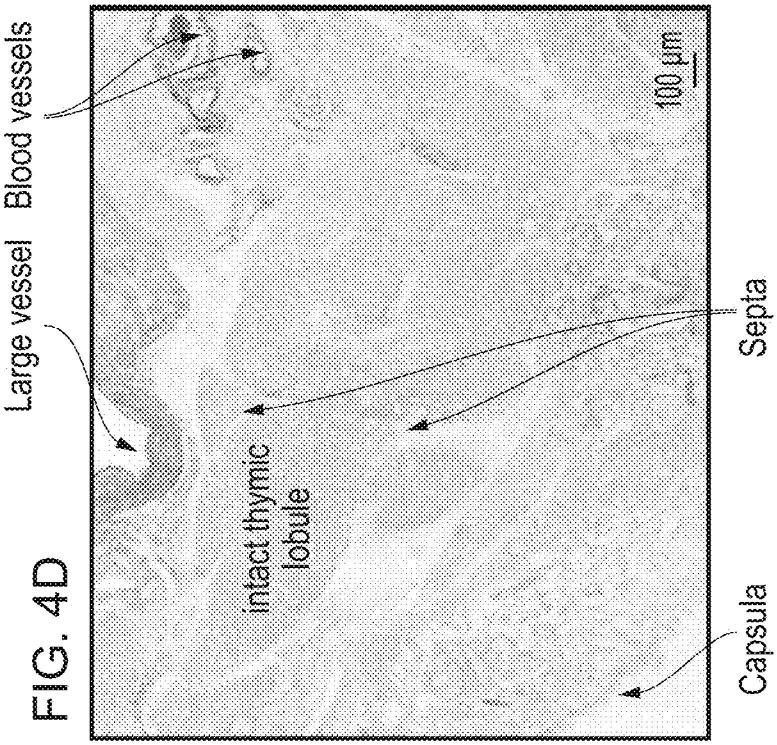

The parallel decellularisation of the thymi illustrates the efficiency and reproducibility of the method of the present invention. As shown in FIG. 2 the decellularisation results in transparent thymic tissue, whilst maintaining the capsule. As shown in FIGS. 2C and 3A, histological analysis of the decellularised thymi by H&E staining demonstrates the absence of any cell nuclei, DNA or cellular debris. FIGS. 3B and C demonstrate preservation of capsular and reticular ECM of the thymus structure. Thymic ECM was detected as a homogenous reticulum and staining intensity reflects the abundance of ECM that is higher in the capsule of the organ (red in FIG. 3B and blue in FIG. 3C).

Example 2

A rat thymus was extracted and decellularised according to the protocol outlined in Example 1. Rat weight was 173 g.

Gross microscopy of the decellularised thymus is shown in FIG. 4 using H&E staining before (4A) and after (4B) decellularisation. Low magnification (FIG. 4C) and an area of higher magnification (FIG. 4D) demonstrates preservation of parenchymal lobular as well as of vascular structures all over the organ tissue. No DNA or cellular debris was detected. This demonstrates whole organ (bi-lobular) decellularisation through a single cannula at histological level.

Example 3

A thymus scaffold was obtained according to the protocol outline in Example 1. The thymus was then repopulated with a 5:1 (respectively) combination of Thymic Epithelial Cells (TEC) and Thymic Mesenchymal Cells (TMC) delivered simultaneously by direct needle injection, following ex vivo expansion from a tissue thymus donor. The cells were injected with a needle syringe (1 injection per lobe, 40p1 each, 2 M TEC: 0.4 M TMC per injection) in the thymic lobes shown as transparent tissue in FIG. 5A-C. Extra thymic tissue (darker areas in FIG. 5A-C) allowed connected to the cannula that was maintained during culture.

Repopulated scaffolds were maintained under in vitro conditions to allow for cell migration over the reticular ECM of the scaffold and initial differentiation (e.g. cell polarization, up/downregulation of adhesion molecules) over a period of 4 days. For in vitro culture the scaffolds were connected to a cannula and placed in a petri dish submerged in cFAD (epithelial) medium, which consists of DMEM and Ham's F12 medium (v/v 3:1), supplemented with 10% foetal bovine serum (FBS), insulin (5 μg/mL), 3,3,5-triiodo-L-thyronine (T3) ($2\times10^{-9}$ M), hydrocortisone (0.4 μg/mL), cholera toxin ($1\times10^{-10}$ M), and 1% penicillin/streptomycin.

Figure 5C:
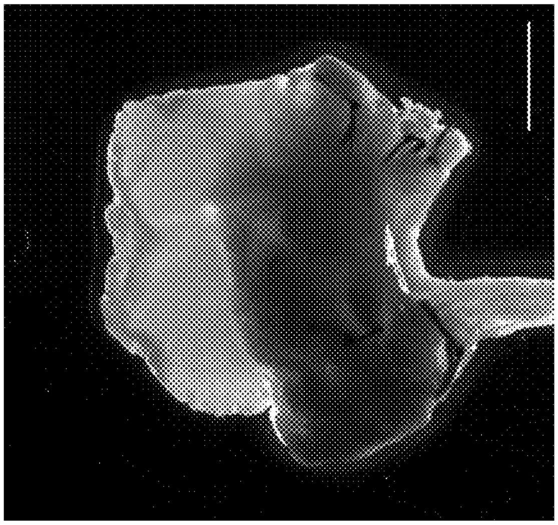
FIGS. 5A-5C show the appearance of a thymus scaffold obtained by the methods of the present invention before (A), soon after (B) and following 4 days of culture (C) after injection of stromal cells. Extra thymic tissue (darker areas in the images) allows connection to the cannula.
Figure 5B:
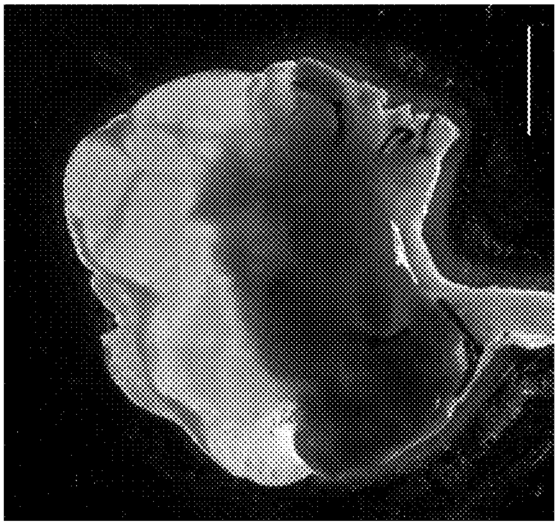
Figure 5A:
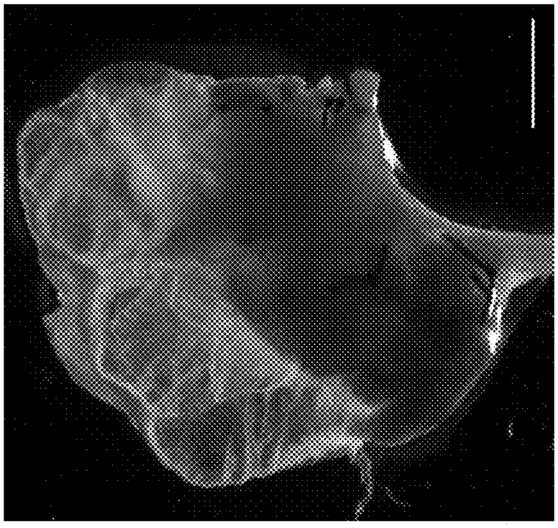
Figure 6A:
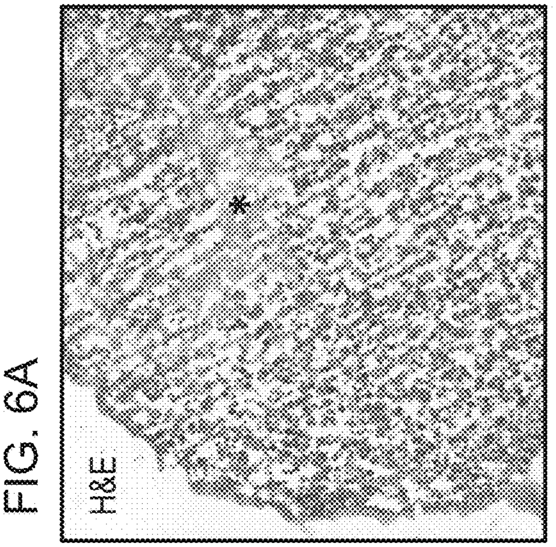
FIGS. 6A-6E show histology (H&E) of the repopulated scaffold cultivated for 4 days (panel A). Immunohistochemistry (IHC) images demonstrate healthy stromal cells, which are negative for Caspase3 and most are positive for progenitor/stem cell marker p63 (panel B). Only few cells (yellow *) are Caspase3-positive indicating apoptosis (panel C). Repopulating stromal cells express Cytokeratin 5 (CK5), CK8 and alpha6 integrin (CD49f) (panel E). Moreover, most epithelial cells (EpCAM-positive) are proliferating (Ki67-positive) (panel D), thus indicating that the stromal cells are repopulating the scaffold and maintain a progenitor phenotype within the 3D structure (Scale bars=50 μm).
Figure 6B:
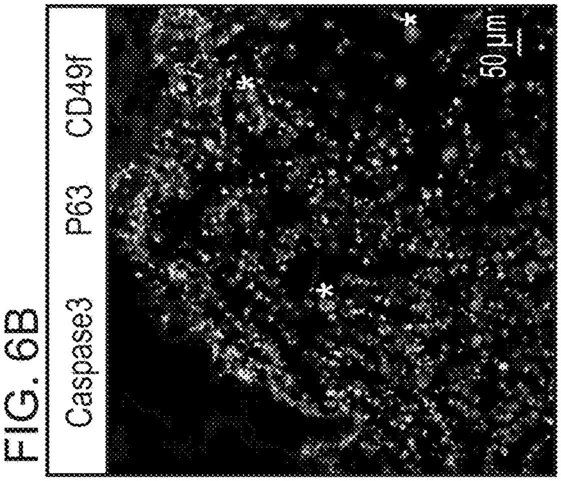
Figure 6C:
Figure 6D:
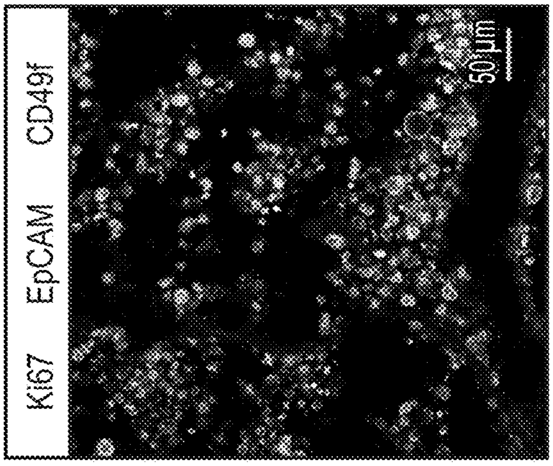
Figure 6E:
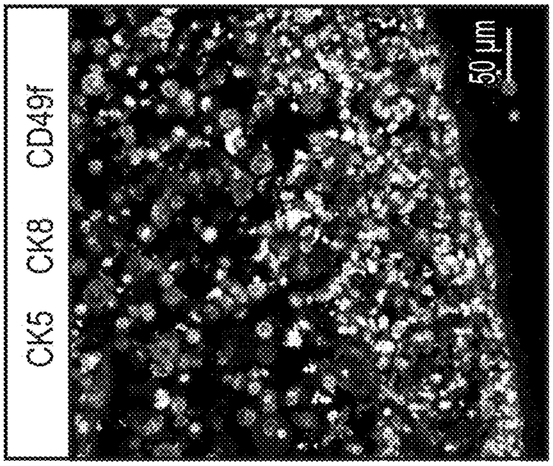

FIG. 5 shows the appearance of the scaffold before (FIG. 5A), soon after (FIG. 5B) and following 4 days of culture after injection of the TEC and TMC cells (FIG. 5C). Histological analysis of the scaffold by H&E staining after 4 days of culture is shown in FIG. 6A, which reveals that cells adhere to and along the scaffold ECM. Only a small area of the scaffold is not yet repopulated, but demonstrates the presence of an intact matrix within the scaffold (black *). Immunohistochemistry (IHC) images demonstrate that healthy stromal cells were negative for Caspase3 and most were positive for progenitor/stem cell marker p63 (FIG. 6B). Only a small number of cells (yellow *) were Caspase3-positive indicating apoptosis (FIG. 6C). Repopulating stromal cells expressed Cytokeratin 5 (CK5), CK8 and alpha6 integrin (CD49f) (FIG. 6E). Moreover, more epithelial cells (EpCAM-positive) were proliferating (Ki67-positive) (FIG. 6D), thus indicating that the stromal cells were repopulating the scaffold and maintaining a progenitor phenotype within the 3D structure.

Example 4

Repopulated rat thymic scaffolds were prepared according to the protocol outlined in Example 3 above. After 4 days of in vitro culture with the stromal cells the repopulated scaffolds were engrafted subcutaneously into NSG mice for 8 and 11 weeks.

Figure 7A:
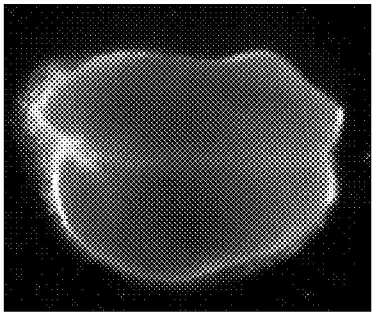
FIGS. 7A-7D show gross macroscopy (panel A, scale bar=2 mm) and histology (H&E) of repopulated scaffolds engrafted in NSG mice and matured in vivo for 8 weeks (B), 11 weeks (C), and 21 weeks (D), respectively. H&E staining demonstrates the presence of small round cells of hematopoietic origin interacting with the organised stromal cells. Notably there is a progressive stromal cell maturation as demonstrated by the presence of Hassall's bodies within the scaffold at 11 weeks' time-point. Scale bars=50 μm.
Figure 7B:
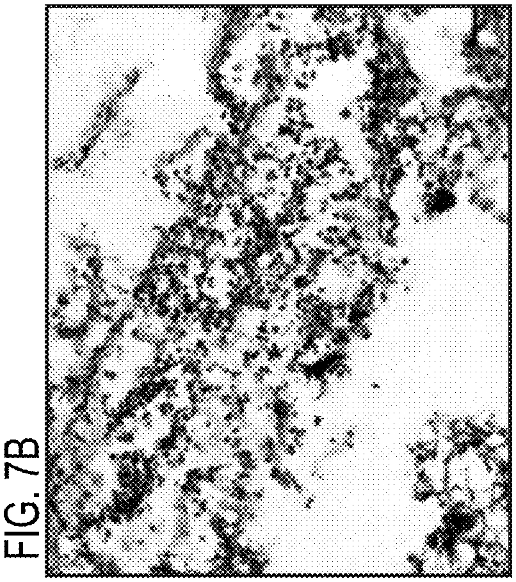
Figure 7C:
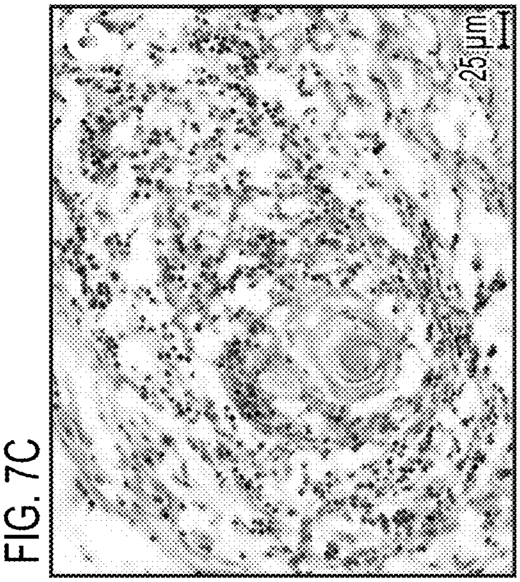
Figure 7D:

Histological analysis (H&E) of the two thymus scaffolds matured in vivo for 8 weeks (FIG. 7B), 11 weeks (FIG. 7C) and 21 weeks (FIG. 7D) demonstrated the presence of small round cells of hematopoietic origin interacting with the organized thymus stromal cells. Notably, there was a progressive stromal cell maturation as demonstrated by the presence of Hassall's bodies within the scaffold at 11 weeks' time-point (FIG. 7C) and increase of thymocyte density (FIG. 7D).

Example 5

Repopulated rat thymic scaffolds were prepared according to the protocol outlined in Example 3 above and were repopulated with human stromal cells identified by EpCAM and ECadherin positive cells. After 4 days of in vitro culture with the stromal cells the repopulated scaffolds were engrafted subcutaneously into NSG mice for 11 weeks.

Figure 8A:
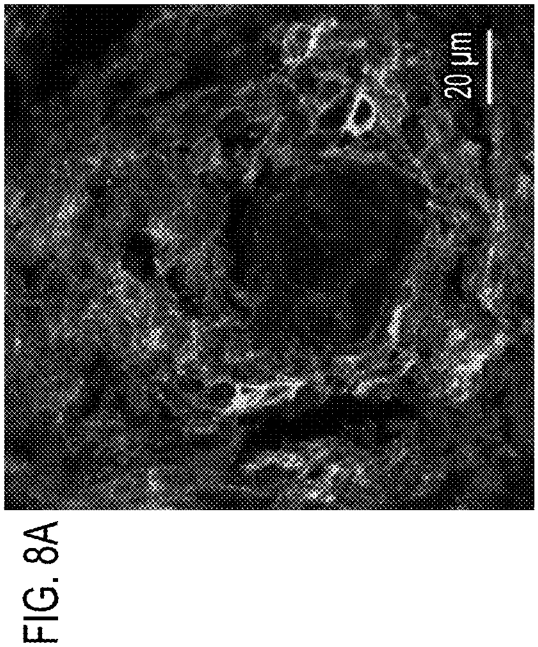
FIGS. 8A-8D show immunohistochemistry of repopulated scaffolds grafted in NSG mice matured in vivo, demonstrating maturation of the human stroma (EpCAM and ECadherin positive cells, red) expressing functional markers such as HLA-DR (green) (A). Anti-Human Vimentin (green) recognises organised human mesenchymal cells (B), while anti-human CD3 (green) demonstrates the presence of maturing thymocytes in contact with human thymus stromal cells (C). Detection of AIRE-1 positive cells (3,3'-Diaminobenzidine, DAB staining) in the grafted thymus scaffolds demonstrates functional maturation of thymus cells, which is important in their role to eliminate self-reactive T cells (D).
Figure 8B:
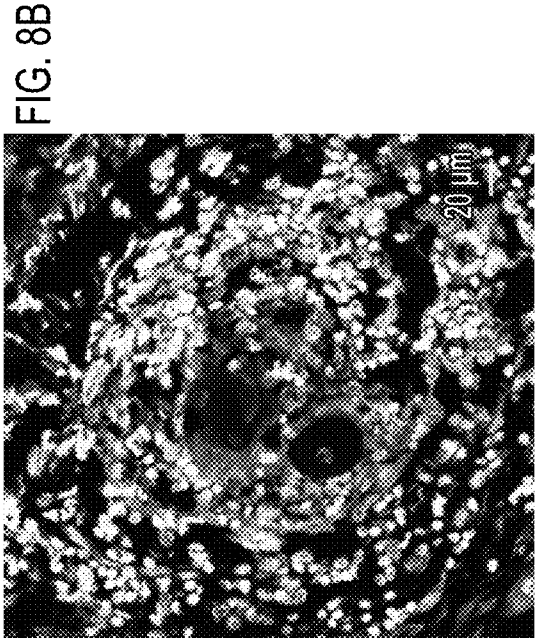
Figure 8C:
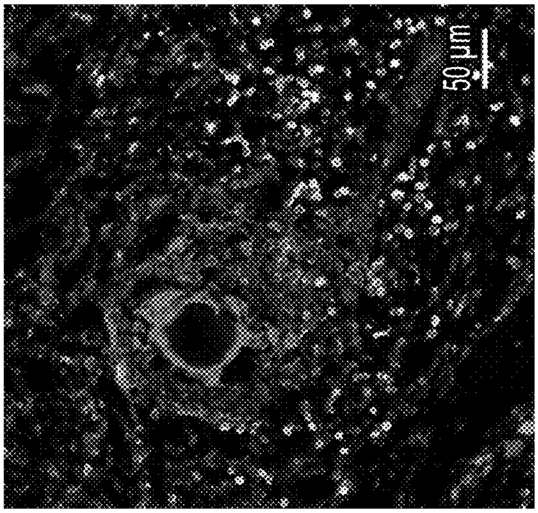
Figure 8D:
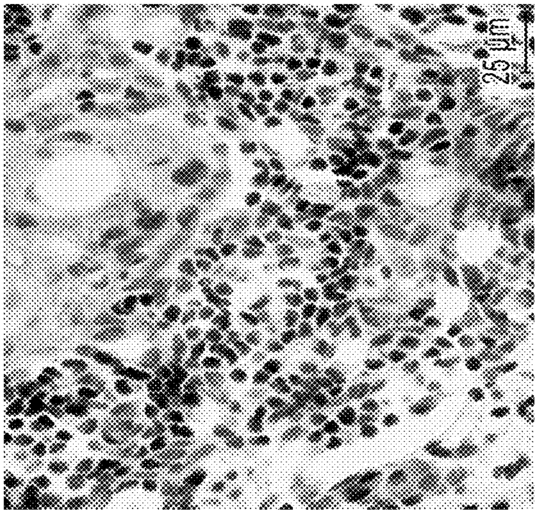

Immunohistochemistry analysis demonstrated the presence of repopulating human stroma identified by EpCAM and ECadherin positive cells. Functional maturation of stromal cells was demonstrated by the up-regulation of MHC Class II surface receptor (HLA-DR-positive cells) (FIG. 8A). Presence of mesenchymal cells was detected by anti-human vimentin immunostaining (FIG. 8B), while anti-human CD3 immunostaining demonstrated the presence of maturing thymocytes within the same area (FIG. 8C). Detection of autoimmune response element 1 (AIRE-1) positive cells in the grafted thymus scaffolds demonstrates functional maturation of thymus cells, which is important in their role to eliminate self-reactive T cells and thereby induce tolerance (FIG. 8D). This demonstrates the capacity of human cultivated stromal cells to survive long term in vivo and organize functional structures similar to the human native thymus (i.e. Hassall's body and expression of HLA-DR).

Example 6

Figure 9A:
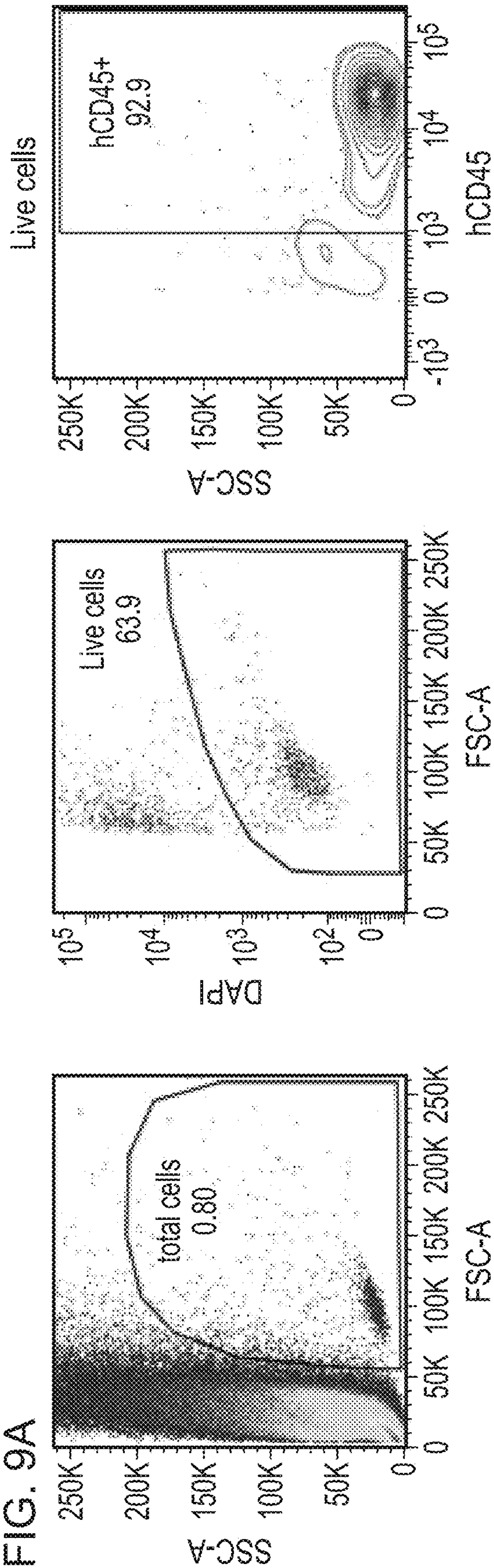
FIGS. 9A-9B show that cells within the repopulated decellularised ECM scaffold differentiate into the correct lymphoid lineages. A. FACS analysis of dissociated human engineered thymus scaffold matured in vivo shows that the vast majority (80%) of CD45+ cells developed from CD34+ progenitors are CD3+, lymphoid lineage; B. Single positive CD4 and CD8 cells express mature markers such as CD3+ and TCRab+.
Figure 9B:
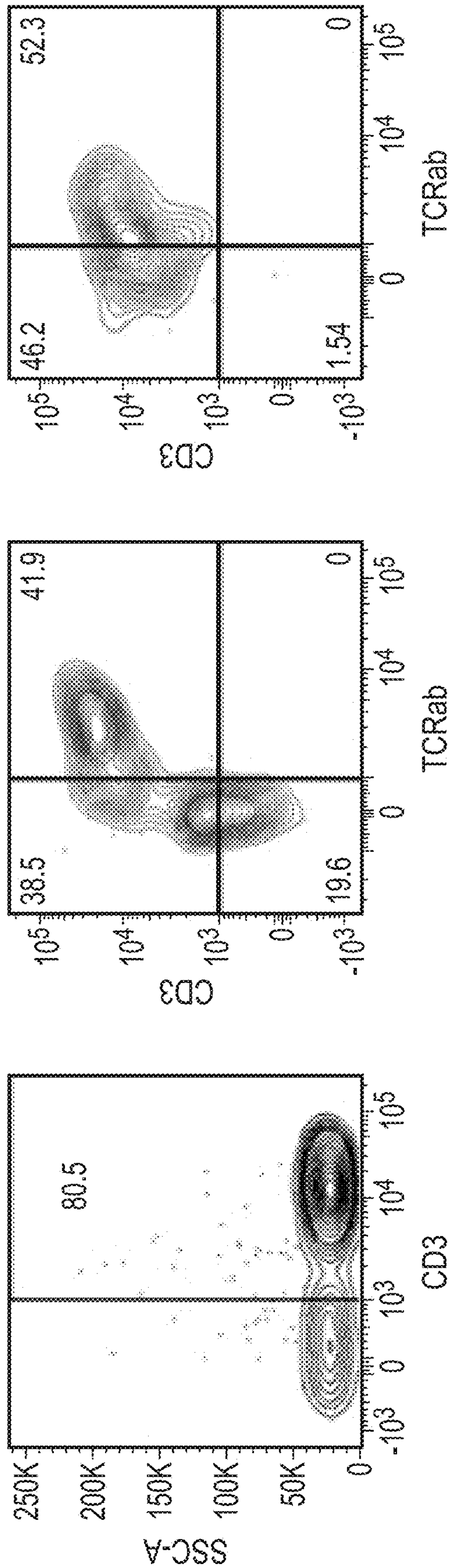

A portion of the thymus scaffolds repopulated and transplanted in vivo into NSG mice, were dissociated and analysed by FACS analysis that demonstrated high survival of human cells (63.9%, middle panel FIG. 9A); the vast majority of live cells were CD45+(92.9%, right panel FIG. 9A). Importantly, 80% of the CD45+ cells were also CD3+(FIG. 9B, left panel) thus demonstrating that the thymus scaffold is an inductive microenvironment for the lymphoid lineage; the presence of single positive CD4+ and CD8+ cells that express TCRab demonstrate that mature functional T cells have been produced within the scaffold in vivo (FIG. 9B, middle and right panels).

Example 7

Figures 10A, 10B:
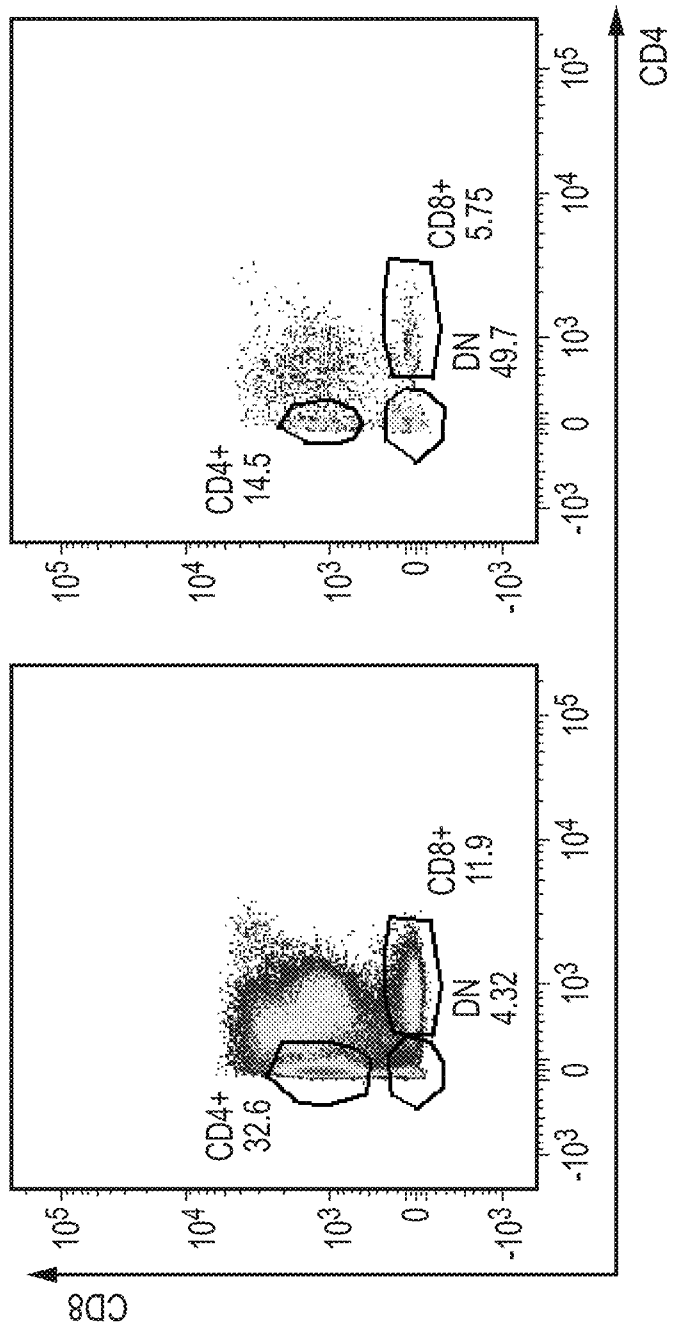
FIGS. 10A-10B show that single and double CD4+ and CD8+ thymocytes are created at proportions equivalent to normal tissue. A. FACS analysis of dissociated fresh human thymus showing single and double positive CD4+ and CD8+ thymocytes. B. FACS analysis of thymocytes developed in vitro from TN progenitors within the engineered thymus scaffold (rat), 6 days' time point; this demonstrates that engineered human thymus supports T cell development ex vivo.
Figure 11:
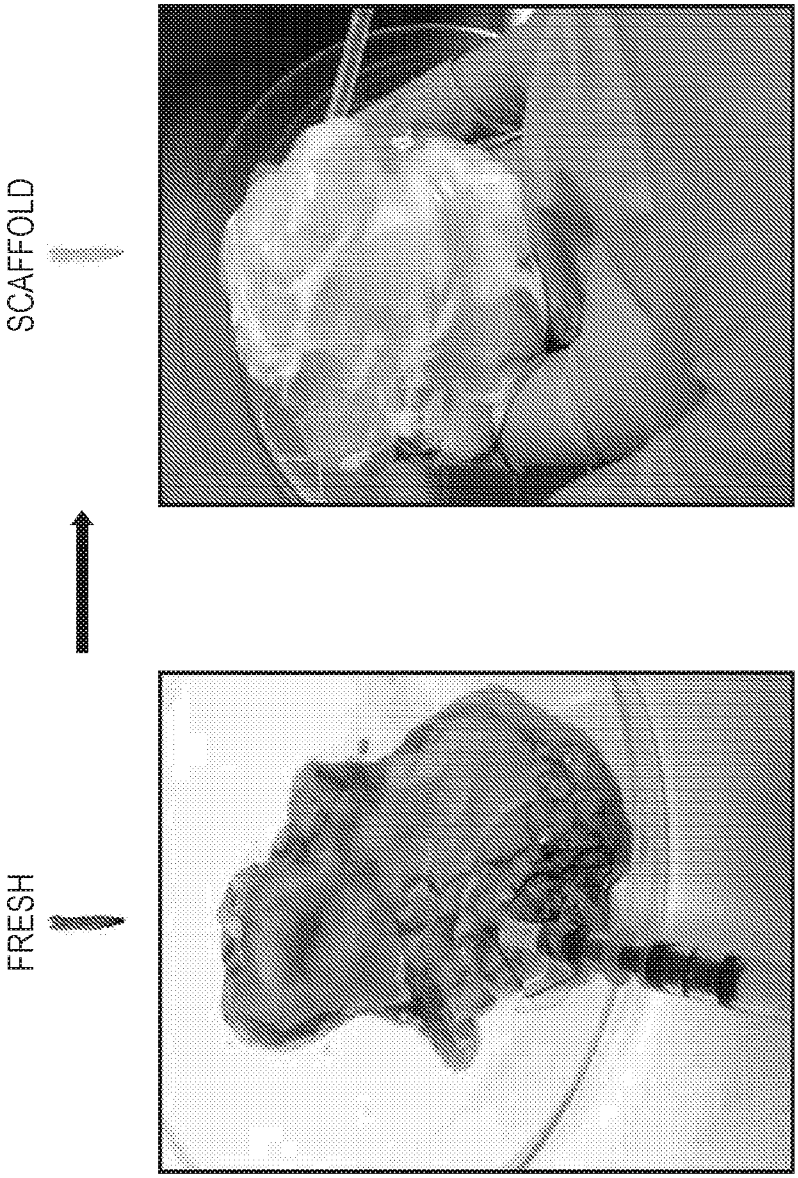
FIG. 11 shows gross microscopy of a pig thymus before (left panel) and after (right panel) perfusion decellularisation (2 cycles of 4 hours perfusion at 4% SDC at 0.6-0.8 ml/min).
Figure 12:
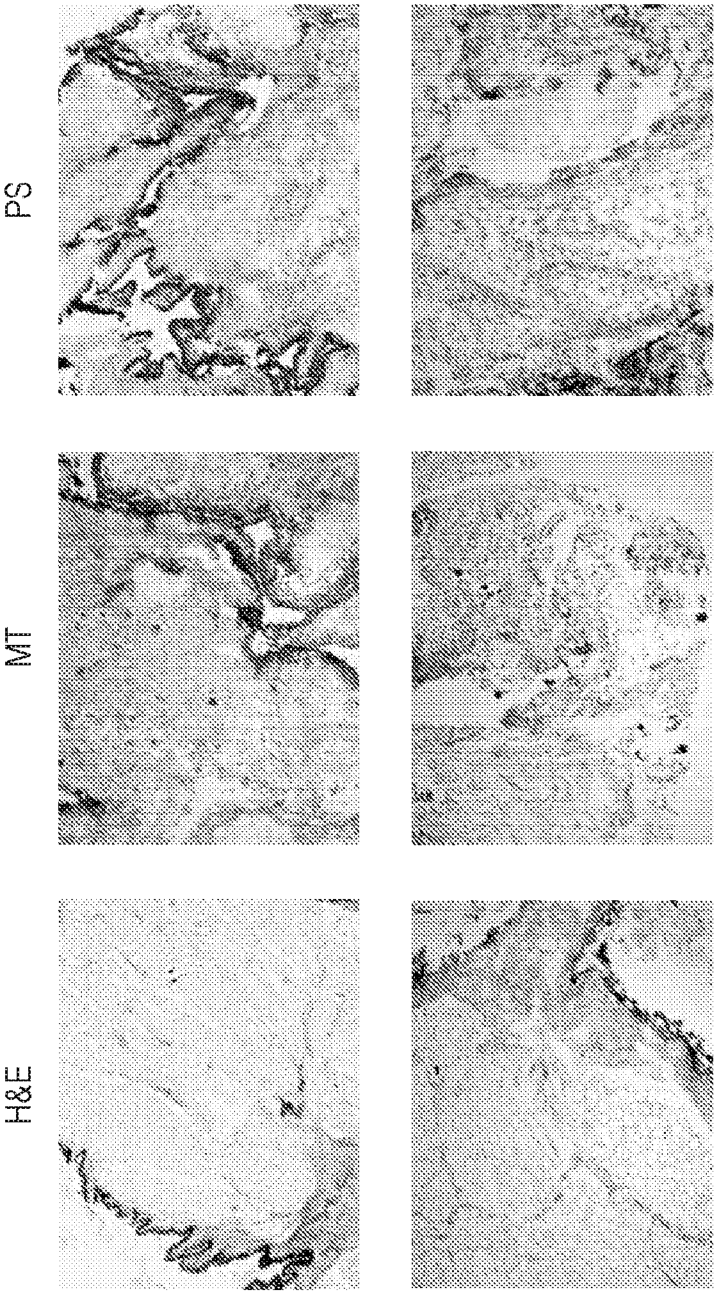
FIG. 12 shows histological analysis of the pig thymus after perfusion-decellularisation demonstrating preservation of ECM and vascular structures: H&E left panel; Masson Trichrome (MT); Picrosirius Red (PS) demonstrate preservation of ECM proteins and vasculature structures.
Figure 13:
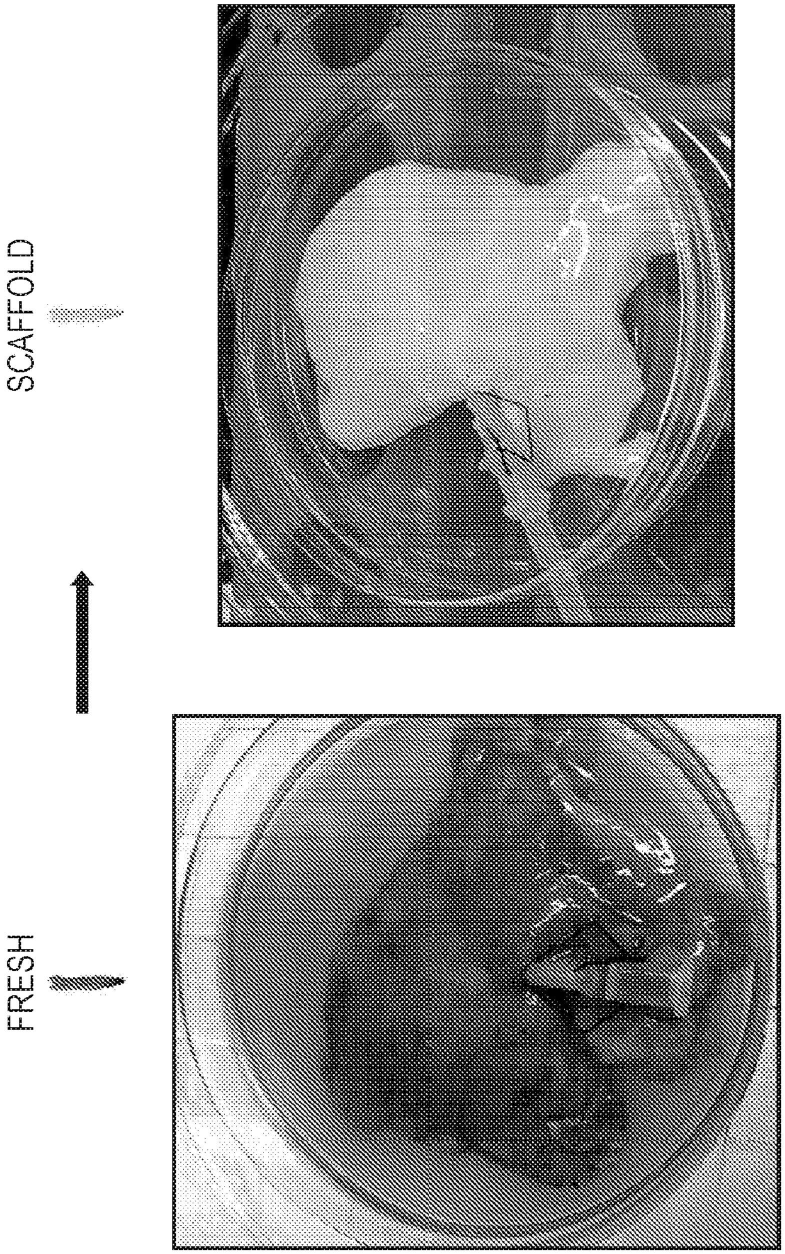
FIG. 13 shows gross microscopy of a human thymus before (left panel) and after (right panel) perfusion decellularisation (2 cycles of 4 hours perfusion at 4% SDC at 0.6-0.8 ml/min).
Figure 14:
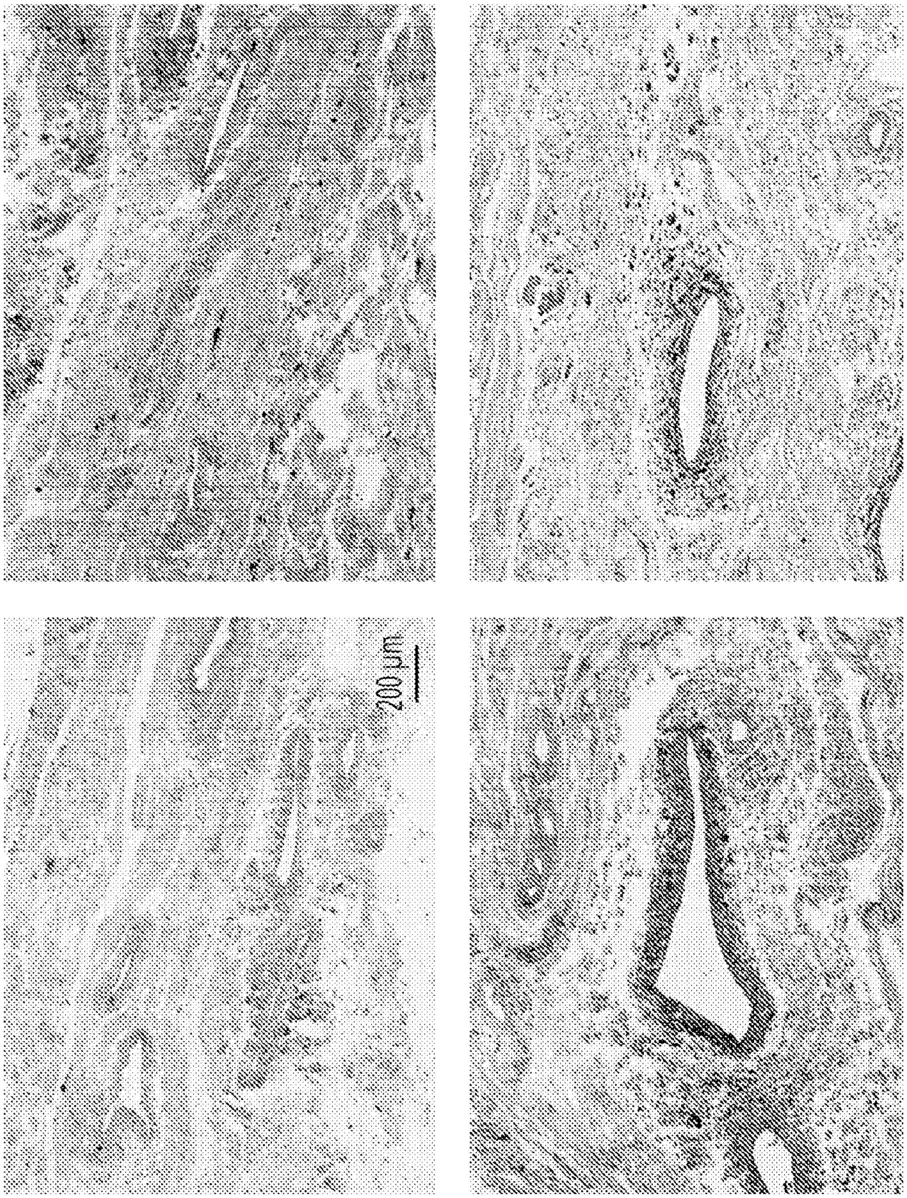
FIG. 14 shows H&E staining of the human thymus scaffold after perfusion decellularisation demonstrating removal of cell components and preservation of large and small vascular structures.

A thymus scaffold was repopulated in vitro with stromal cells, and maintained in culture for 7 days before being injected with immature triple negative thymocytes (TN). The thymocytes were analysed by FACS 7 days after injection into the thymus scaffold where they matured towards both single and double positive CD4+ and CD8+ cells (FIG. 10B). Importantly the ratio of single positive CD4/CD8 in the scaffold is similar to the native thymus (FIG. 10A,B).

The project leading to this application has received funding from the European Union's Horizon 2020 research and innovation programme under grant agreement no. 639429.

REFERENCES

Fan Y., Tajima A., Goh S K., Geng X., Gualtierottii G., Grupillo M., Coppola A., Bertera S., Rudert W A., Banerjee I., Bottino R., Trucco M. Bioengineering Thymus Organoids to Restore Thymic Function and Induce Donor-Specific Immune Tolerance to Allografts, Molecular Therapy 2015; 23:1262-1277

Goh S K., Bertera S., Olsen P., Candiello J., Halfter W., Uechi G., Balasubramani M., Johnson S., Sicari B., Kollar E., Badylak S F., Banerjee I. Perfusion-decellularised pancreas as a natural 3D scaffold for pancreatic tissue and whole organ engineering. Biomaterials 2013; 34(28): 6760-6772

Katari R., Peloso A., Zambon J P., Sokeer S., Stratta R J., Atala A., Orlando G. Renal Bioengineering with Scaffolds Generated from Human Kidneys, Nephron Exp. Nephrol. 2014; 126:119-124

The invention claimed is:

1. A method of producing a decellularised extracellular matrix (ECM) scaffold of at least a portion of a lobular organ with no common artery, the method comprising:

a) closing afferent blood vessels to substantially seal a target lobular organ, or a portion thereof, with no common artery within a non-human donor or a dead/brain dead human donor;

b) optionally: (i) cleaning coagulum and/or blood from at least a portion of the closed afferent blood vessels; and/or (ii) perfusing the target lobular organ or the portion thereof to confirm closure of the afferent blood vessels to form a sealed organ or sealed portion thereof;

c) removing the sealed organ or the sealed portion thereof from the non-human donor or the dead/brain dead human donor; and d) perfusing the sealed organ or the sealed portion thereof with a detergent and enzymatic solutions to obtain the decellularised ECM scaffold.

2. The method according to claim 1, wherein the detergent is sodium deoxycholate (SDC), sodium dodecyl sulphate (SDS), Triton X-100, or a combination thereof.

3. The method according to claim 2, wherein the SDC concentration is about 1% to about 10% (w/v), or the SDS concentration is about 0.05% to about 1% (w/v), or the Triton X-100 concentration is about 0.05% to about 5% (w/v).

4. The method according to claim 1, wherein the sealed organ or the portion thereof is perfused with the detergent for about 1 to about 4 hours.

5. The method according to claim 1, wherein the sealed organ or the portion thereof is perfused with the detergent at a rate from about 0.2 ml/min to about 1 ml/min.

6. The method according to claim 1, wherein the sealed organ or the portion thereof is perfused for a single cycle.

7. The method according to claim 1, wherein the sealed organ or the portion thereof is freely floating in solution during perfusion.

8. The method according to claim 1, wherein the lobular organ, or the portion thereof, with no common artery is a) a thymus or a lobe thereof, b) a thyroid gland or a lobe thereof, c) a parathyroid gland or d) a salivary gland.

9. The method according to claim 8, wherein the lobular organ is the thymus, and wherein the afferent blood vessels closed to seal the thymus comprise a right or left common carotid artery, a right subclavian artery, a right internal mammary artery, a right costocervical trunk, a right aortic arch, a left aortic arch, a left costocervical trunk, a left internal mammary artery and a left subclavian artery, a left internal mammary artery, a left costocervical trunk and a left aortic arch in the non-human donor or the dead/brain dead human donor.

10. The method according to claim 9, wherein the right common carotid artery is closed and the thymus is perfused through the left common carotid artery, or wherein the left common carotid artery is closed and the thymus is perfused through the right common carotid artery.

11. The method according to claim 8, wherein the blood vessels closed to seal the thyroid comprise the right or left common carotid artery following a junction with a superior thyroid artery.

12. The method according to claim 11, wherein each thyroid lobe is perfused through the right or left common carotid artery.

13. A method for producing an artificial organ, the method comprising:

i) producing a decellularised extracellular matrix (ECM) scaffold of at least a portion of a lobular organ with no common artery, the method comprising:

a) closing afferent blood vessels to substantially seal a target lobular organ, or a portion thereof, with no common artery within a non-human donor or a dead/brain dead human donor;

b) optionally: (i) cleaning coagulum and/or blood from at least a portion of the closed afferent blood vessels; and/or (ii) perfusing the target lobular organ or the or sealed portion thereof to confirm closure of the afferent blood vessels to form a sealed organ;

c) removing the sealed organ or the sealed portion thereof from the non-human donor or the dead/brain dead human donor; and d) perfusing the sealed organ or the sealed portion thereof with a detergent and enzymatic solutions to obtain the decellularised ECM scaffold;

ii) repopulating the decellularised ECM scaffold with stromal cells, to form a repopulated scaffold, and iii) culturing the repopulated scaffold in vitro for about 4 to about 7 days, thereby producing the artificial organ.

14. The method according to claim 13, wherein the stromal cells are a combination of epithelial and mesenchymal cells, and wherein the decellularized ECM scaffold is repopulated with the epithelial and mesenchymal cells at a ratio of about 2:1 to about 5:1.

15. The method according to claim 13, further comprising seeding the repopulated scaffold with donor cells.

* * * * *